(12) United States Patent
Amphlett et al.

(10) Patent No.: US 7,514,080 B2
(45) Date of Patent: Apr. 7, 2009

(54) DRUG CONJUGATE COMPOSITION

(75) Inventors: Godfrey Amphlett, Cambridge, MA (US); Wei Zhang, Cambridge, MA (US); Michael Fleming, Londonderry, NH (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 11/520,878

(22) Filed: Sep. 14, 2006

(65) Prior Publication Data

US 2007/0009539 A1 Jan. 11, 2007

Related U.S. Application Data

(62) Division of application No. 10/846,129, filed on May 14, 2004, now Pat. No. 7,374,762.

(60) Provisional application No. 60/470,550, filed on May 14, 2003.

(51) Int. Cl.
*A61K 39/00* (2006.01)
*A61K 39/395* (2006.01)
*A61K 39/44* (2006.01)

(52) U.S. Cl. .............. 424/133.1; 424/141.1; 424/142.1; 424/178.1; 424/184.1; 424/193.1

(58) Field of Classification Search ........................ None
See application file for complete search history.

(56) References Cited

U.S. PATENT DOCUMENTS

| | | | |
|---|---|---|---|
| 3,896,111 A | 7/1975 | Kupchan et al. | |
| 4,151,042 A | 4/1979 | Higashide et al. | |
| 4,563,304 A | 1/1986 | Carlsson et al. | |
| 5,208,020 A | 5/1993 | Chari et al. | |
| 5,225,539 A | 7/1993 | Winter | |
| 5,416,064 A | 5/1995 | Chari et al. | |
| 5,475,092 A | 12/1995 | Chari et al. | |
| 5,545,806 A | 8/1996 | Lonberg et al. | |
| 5,569,825 A | 10/1996 | Lonberg et al. | |
| 5,585,089 A | 12/1996 | Queen et al. | |
| 5,639,641 A | 6/1997 | Pedersen et al. | |
| 5,665,357 A | 9/1997 | Rose et al. | |
| 5,693,761 A | 12/1997 | Queen et al. | |
| 5,714,352 A | 2/1998 | Jakobovits | |
| 6,171,586 B1 | 1/2001 | Lam et al. | |
| 6,265,150 B1 | 7/2001 | Terstappen et al. | |
| 6,333,410 B1 | 12/2001 | Chari et al. | |
| 6,340,701 B1 | 1/2002 | Chari et al. | |
| 6,372,738 B2 | 4/2002 | Chari et al. | |
| 6,436,931 B1 | 8/2002 | Chari et al. | |
| 6,441,163 B1 | 8/2002 | Chari et al. | |
| 6,716,821 B2 | 4/2004 | Zhao et al. | |
| 6,756,397 B2 | 6/2004 | Zhao et al. | |
| 6,824,780 B1 | 11/2004 | Devaux et al. | |
| 2001/0036923 A1 | 11/2001 | Chari et al. | |
| 2002/0001587 A1 | 1/2002 | Erickson et al. | |
| 2002/0197266 A1 | 12/2002 | Debinski | |
| 2003/0004210 A1 | 1/2003 | Chari et al. | |

FOREIGN PATENT DOCUMENTS

| | | |
|---|---|---|
| EP | 0 239 400 B1 | 8/1994 |
| GB | 2 188 638 A | 10/1987 |
| WO | WO 97/04801 A1 | 2/1997 |
| WO | WO 00/02587 A1 | 1/2000 |
| WO | WO 01/00244 A2 | 1/2001 |
| WO | WO 01/24763 A2 | 4/2001 |
| WO | WO 01/38318 A1 | 5/2001 |
| WO | WO 01/49698 A1 | 7/2001 |
| WO | WO 02/16401 A2 | 2/2002 |
| WO | WO 02/060955 A2 | 8/2002 |
| WO | WO 02/092127 A1 | 11/2002 |
| WO | WO 03/057163 A2 | 7/2003 |
| WO | WO 03/097625 A1 | 11/2003 |

OTHER PUBLICATIONS

Lepage et al., *American Assn. for Cancer Research (AACR)*, 2003 Annual Meeting, Poster Abstract 749.
Bartnes, *Tidsskr. Nor. Laegforen.*, 121,2941-2945 (2001).
Behm et al., *Blood*, 87, 1134-1139 (1996).
Carlsson et al., *Biochemical Journal*, 173, 723-737 (1978).
Chang et al., *Cancer Res.* 59, 3192-3198 (1999).
Colomer et al., *Cancer Investigation*, 19 (1), 49-56 (2001).
Francisco et al., *Blood*, 102 (4), 1458-1465 (2003).
Ghetie et al., *Journal of Immunological Methods*, 112, 267-277 (1988).
Haskard et al., *J. Immunol. Methods*, 74(2), 361-367 (1984).
Heider et al., *European Journal of Cancer*, 31A (13/14), 2385-2391 (1995).
Huse et al., *Science*, 246, 1275-1281 (1989).
Ichimura et al., *Journal of Antibiotics*, 44 (10), 1045-1053 (1991).
Kearse et al., *Int. J. Cancer*, 88, 866-872 (2000).
Kohler et al., *Eur. J. Immunol.*, 5, 511-519 (1976).
Kupchan et al., *Journal of Medicinal Chemistry*, 21 (1), 31-37 (1978).
Liu et al., *Proc. Natl. Acad. Sci*, 93, 8618-8623 (1996).
Maloney et al., *Blood*, 90 (6), 2188-2195 (1997).
Miotti et al., *Int. J. Cancer*, 39, 297-303 (1987).
Nadler et al., *Journal of Immunology*, 131 (1), 244-250 (1983).
Pedersen et al., *Journal of Molecular Biology*, 235 (3), 959-973 (1994).
Reiter et al., *Protein Engineering*, 7 (5), 697-704 (1994).
Remillard et al., *Science*, 189 (4207), 1002-1005 (1975).
Roder et al., *Methods Enzymol.*, 121, 140-167 (1986).
Roguska et al., *Proc. Natl. Acad. Sci.*, 969-973 (1994).
Sasse et al., *Journal of Antibiotics*, 53 (9), 879-885 (2000).
Suzawa et al., *Bioorganic and Medicinal Chemistry*, 8, 2175-2184 (2000).
Von Mensdorff-Pouilly et al., *Int. J. Biol. Markers*, 15, 343-356 (2000).
Wang, *International Journal of Pharmaceutics*, 203, 1-60 (2000).
Welt et al., *Journal of Clinical Oncology*, 12 (6), 1193-1203 (1994).
Yoshitake et al., *European Journal of Biochemistry*, 101, 395-399 (1979).
Baeckstrom et al., *The Journal of Biological Chemistry*, 266(32): 21537-21547 (1991).

*Primary Examiner*—Phuong Huynh
(74) *Attorney, Agent, or Firm*—Leydig, Voit & Mayer, Ltd.

(57) ABSTRACT

The invention provides a liquid composition and a lyophilized composition comprising a therapeutically effective amount of a conjugate comprising an antibody chemically coupled to a maytansinoid. The invention further provides a method for killing a cell in a human comprising administering to the human either of the compositions such that the antibody binds to the surface of the cell and the cytotoxicity of the maytansinoid is activated, whereby the cell is killed.

102 Claims, No Drawings

DRUG CONJUGATE COMPOSITION

CROSS-REFERENCE TO RELATED PATENT APPLICATIONS

This patent application is a divisional of U.S. patent application Ser. No. 10/846,129, filed May 14, 2004, which claims the benefit of U.S. Provisional Patent Application No. 60/470,550, filed May 14, 2003.

FIELD OF THE INVENTION

This invention pertains to a conjugate comprising an antibody chemically coupled to a maytansinoid, and methods of using same.

BACKGROUND OF THE INVENTION

The treatment of cancer has progressed significantly with the development of pharmaceuticals that more efficiently target and kill cancer cells. To this end, researchers have taken advantage of cell-surface receptors and antigens selectively expressed by cancer cells to develop drugs based on antibodies that bind the tumor-specific or tumor-associated antigens. In this regard, cytotoxic molecules such as bacteria and plant toxins, radionuclides, and certain chemotherapeutic drugs have been chemically linked to monoclonal antibodies that bind tumor-specific or tumor-associated cell surface antigens (see, e.g., International (PCT) Patent Application Nos. WO 00/02587, WO 02/060955, and WO 02/092127, U.S. Pat. Nos. 5,475,092, 6,340,701, 6,171,586, U.S. Patent Application Publication No. 2003/0004210 A1, and Ghetie et al., *J. Immunol. Methods*, 112, 267-277 (1988)). Such compounds are typically referred to as toxin, radionuclide, and drug "conjugates," respectively. Often they also are referred to as immunoconjugates, radioimmunoconjugates and immunotoxins. Tumor cell killing occurs upon binding of the drug conjugate to a tumor cell and activation of the cytotoxic activity of the maytansinoid. The selectivity afforded by drug conjugates minimizes toxicity to normal cells, thereby enhancing tolerability of the drug in the patient.

Despite the tumor selectivity afforded by drug conjugates, the use of drug conjugates in a clinical context is limited by a number of factors. In this respect, drug conjugate formulations typically are based on a known formulation of the antibody from which the drug conjugate is manufactured, without consideration as to what effect the conjugated cytotoxic molecule may have on the stability of the antibody. As such, current drug conjugate compositions are less stable than compositions containing the tumor-specific antibody alone.

Thus, in view of the above, there remains a need for drug conjugate compositions containing highly cytotoxic drugs that are more stable than currently available drug conjugate compositions. There also remains a need for methods of using such drug conjugate compositions to treat human diseases associated with cell proliferation, such as cancer.

The invention provides such a composition and method. These and other advantages of the invention, as well as additional inventive features, will be apparent from the description of the invention provided herein.

BRIEF SUMMARY OF THE INVENTION

The invention provides a composition comprising (i) a therapeutically effective amount of a conjugate comprising an antibody chemically coupled to a maytansinoid, (ii) a buffering agent, (iii) a tonicifying amount of sodium chloride, (iv) water, and optionally (v) a surfactant, wherein the composition has a pH of about 5-6. The invention also provides a lyophilized composition comprising (i) a therapeutically effective amount of a conjugate comprising an antibody chemically coupled to a maytansinoid, (ii) a buffering agent, (iii) a cryoprotectant, (iv) a bulking agent, and optionally (v) a surfactant, wherein the composition has a pH of about 5-6 when reconstituted with water. The invention further provides a method for killing a cell in a human comprising administering to the human either of the above-described compositions such that the antibody binds to the surface of the cell and the cytotoxicity of the maytansinoid is activated, whereby the cell is killed.

DETAILED DESCRIPTION OF THE INVENTION

The invention provides a composition comprising (i) a therapeutically effective amount of a conjugate comprising an antibody chemically coupled to a maytansinoid, (ii) a buffering agent, (iii) optionally a surfactant, (iv) a tonicifying amount of sodium chloride, and (v) water, wherein the composition has a pH of about 5-6.

The inventive composition contains a conjugate which comprises an antibody chemically coupled to a maytansinoid. The term "antibody," as used herein, refers to any immunoglobulin, any immunoglobulin fragment, such as Fab, F(ab')$_2$, dsFv, sFv, diabodies, and triabodies, or immunoglobulin chimera, which can bind to an antigen on the surface of a cell (e.g., which contains a complementarity determining region (CDR)). Any suitable antibody can be used in the inventive composition. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secrete a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, *J. Immunol. Methods*, 74(2), 361-67 (1984), and Roder et al., *Methods Enzymol.*, 121, 140-67 (1986)), or bacteriophage vector expression systems (see, e.g., Huse et al., *Science*, 246, 1275-81 (1989)). To prepare monoclonal antibody fragments, recombinant methods typically are employed.

The monoclonal antibody can be isolated from or produced in any suitable animal, but is preferably produced in a mammal, more preferably a mouse, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-drug conjugate. To circumvent these complications, a monoclonal antibody preferably is not recognized as "foreign" by the human immune system. To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example U.S. Pat. Nos. 5,545,806 and 5,569,825, and Janeway et al., supra. Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225, 539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994). While the antibody employed in the conjugate of the inventive composition most preferably is a humanized monoclonal antibody, a human monoclonal antibody or a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab')$_2$ fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the present invention, however, are not limited to these exemplary types of antibody fragments. Any suitable antibody fragment that recognizes and binds to a desired cell surface receptor or antigen can be employed. Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

In addition, the antibody can be a chimeric antibody. By "chimeric" is meant that the antibody comprises at least two immunoglobulins, or fragments thereof, obtained or derived from at least two different species (e.g., two different immunoglobulins, a human immunoglobulin constant region combined with a murine immunoglobulin variable region).

Any suitable antibody can be used in the inventive composition. Particularly preferred antibodies are humanized monoclonal antibodies, examples of which include huN901, huMy9-6, huB4, huC242, trastuzumab, bivatuzumab, sibrotuzumab, and rituximab (see, e.g., U.S. Pat. No. 5,639,641, U.S. Provisional Patent Application No. 60/424,332, International (PCT) Patent Application No. WO 02/16401, Pedersen et al., *J. Mol. Biol.*, 235, 959-973 (1994), Roguska et al., *Proc. Natl. Acad. Sci. USA*, 91, 969-73 (1994), Liu et al., *Proc. Natl. Acad. Sci. USA*, 93, 8618-8623 (1996), Nadler et al., *J. Immunol.*, 131, 244-250 (1983), Colomer et al., *Cancer Invest.*, 19, 49-56 (2001), Heider et al., *Eur. J. Cancer*, 31A, 2385-2391 (1995), Welt et al., *J. Clin. Oncol.*, 12, 1193-1203 (1994), Maloney et al., *Blood*, 90, 2188-2195 (1997), and U.S. Pat. No. 5,665,357). Most preferably, the antibody is the huN901 humanized monoclonal antibody or the huMy9-6 humanized monoclonal antibody. Other humanized monoclonal antibodies are known in the art and can be used in connection with the inventive composition.

In accordance with the invention, the above-described antibody is chemically coupled to any suitable cytotoxic agent, particularly a cytotoxic agent that induces cytotoxicity of tumor cells, to form a conjugate as described above. As a result of normal pharmacologic clearance mechanisms, an antibody employed in a drug conjugate contacts and binds to target cells only in limited amounts. Therefore, the cytotoxic agent employed in the conjugate must be highly cytotoxic such that sufficient cell killing occurs to elicit a therapeutic effect. Examples of such cytotoxic agents include novel taxanes (see, e.g., International (PCT) Patent Application Nos. WO 01/38318 and PCT/US03/02675), DNA-alkylating agents (e.g., CC-1065 analogs), anthracyclines, tubulysin analogs, duocarmycin analogs, auristatin E, and cytotoxic agents comprising a reactive polyethylene glycol moiety (see, e.g., Sasse et al., *J. Antibiot.* (Tokyo), 53, 879-85 (2000), Suzawa et al., *Bioorg. Med. Chem.*, 8, 2175-84 (2000), Ichimura et al., *J. Antibiot.* (Tokyo), 44, 1045-53 (1991), Francisco et al., *Blood* (2003) (electronic publication prior to print publication), U.S. Pat. Nos. 5,475,092, 6,340,701, 6,372,738, and 6,436,931, U.S. Patent Application Publication No. 2001/0036923 A1, Pending U.S. patent application Ser. Nos. 10/024,290 and 10/116,053, and International (PCT) Patent Application No. WO 01/49698). Alternatively and most preferably, the antibody is chemically coupled to a maytansinoid to form the conjugate of the inventive composition.

Maytansinoids were originally isolated from the east African shrub belonging to the genus *Maytenus,* but were subsequently also discovered to be metabolites of soil bacteria, such as *Actinosynnema pretiosum* (see, e.g., U.S. Pat. No. 3,896,111). Maytansinoids induce cytotoxicity through mitotic inhibition. Experimental evidence suggests that maytansinoids inhibit mitosis by inhibiting polymerization of the microtubule protein tubulin, thereby preventing formation of microtubules (see, e.g., U.S. Pat. No. 6,441,163 and Remillard et al., *Science,* 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020). Maytansinoids are known in the art to include maytansine, maytansinol, C-3 esters of maytansinol, and other maytansinol analogues and derivatives (see, e.g., U.S. Pat. Nos. 5,208,020 and 6,441,163). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues also are known in the art and described in, for example, Kupchan et al., *J. Med. Chem.,* 21, 31-37 (1978). Methods for generating maytansinol and analogues and derivatives thereof are described in, for example, U.S. Pat. No. 4,151,042.

Suitable maytansinoids for use in the inventive composition can be isolated from natural sources, synthetically produced, or semi-synthetically produced using methods known in the art. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate. The linking moiety contains a chemical bond that allows for the activation of maytansinoid cytotoxicity at a particular site. Suitable chemical bonds are well known in the art and include disulfide bonds, acid labile bonds, photolabile bonds, peptidase labile bonds, thioether bonds formed between sulfhydryl and maleimide groups, and esterase labile bonds. Most preferably, the linking moiety comprises a disulfide bond or a thioether bond. In accordance with the invention, the linking moiety preferably comprises a reactive chemical group. Particularly preferred reactive chemical groups are N-succinimidyl esters and N-sulfosuccinimidyl esters. In a preferred embodiment, the reactive chemical group can be covalently bound to the maytansinoid via disulfide bonding between thiol groups. Thus, a maytansinoid modified as described herein preferably comprises a thiol group. One of ordinary skill in the art will appreciate that a thiol group contains a sulfur atom bonded to a hydrogen atom and is typically also referred to in the art as a sulfhydryl group, which can be denoted as "—SH" or "RSH."

Particularly preferred maytansinoids comprising a linking moiety that contains a reactive chemical group are C-3 esters of maytansinol and its analogs where the linking moiety contains a disulfide bond and the chemical reactive group comprises a N-succinimidyl or N-sulfosuccinimidyl ester. Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol. Most preferably, the maytansinoid used in connection with the inventive composition is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)-maytansine (DM4).

Linking moieties with other chemical bonds also can be used in the context of the invention, as can other maytansinoids. Specific examples of other chemical bonds include acid labile bonds, thioether bonds, photolabile bonds, peptidase labile bonds and esterase labile bonds. Methods for producing maytansinoids with linking moieties are described in, for example, U.S. Pat. Nos. 5,208,020, 5,416,064, and 6,333,410.

The linking moiety of a maytansinoid typically and preferably is part of a larger linker molecule that is used to join the antibody to the maytansinoid. Any suitable linker molecule can be used in connection with the invention, so long as the linker molecule provides for retention of the cytotoxicity and targeting characteristics of the maytansinoid and the antibody, respectively. The linker molecule joins the maytansinoid to the antibody through chemical bonds (as described above), such that the maytansinoid and the antibody are chemically coupled (e.g., covalently bonded) to each other. Desirably, the linker molecule chemically couples the maytansinoid to the antibody through disulfide bonds or thioether bonds. Most preferably, the antibody is chemically coupled to the maytansinoid via disulfide bonds.

Particularly preferred linker molecules include, for example, N-succinimidyl 3-(2-pyridyldithio)propionate (SPDP) (see, e.g., Carlsson et al., *Biochem. J.,* 173, 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), N-succinimidyl 4-(N-maleimidomethyl)cyclohexane-1-carboxylate (SMCC) (see, e.g., Yoshitake et al., *Eur. J. Biochem.*, 101, 395-399 (1979)), and N-succinimidyl 4-methyl-4-[2-(5-nitro-pyridyl)-dithio]pentanoate (SMNP) (see, e.g., U.S. Pat. No. 4,563,304) The most preferred linker molecules for use in the inventive composition are SPP, SMCC, and SPDB.

The inventive composition comprises a therapeutically effective amount of a conjugate comprising an antibody chemically coupled to a maytansinoid. A "therapeutically effective amount" means an amount sufficient to show a meaningful benefit in an individual, e.g., promoting at least one aspect of tumor cell cytotoxicity, or treatment, healing, prevention, or amelioration of other relevant medical condition(s) associated with a particular cancer. Therapeutically effective amounts may vary depending upon the biological effect desired in the individual, condition to be treated, and/or the specific characteristics of the conjugate, and the individual. Thus, in accordance with the methods described herein, the attending physician (or other medical professional responsible for administering the composition) will typically decide the amount of the composition with which to treat each individual patient. The concentration of the conjugate in the inventive composition desirably is about 0.1 mg/mL to about 5 mg/mL (e.g., about 0.5 mg/mL, about 2 mg/mL, or about 5 mg/mL). In a preferred embodiment, the concentration of the conjugate in the inventive composition is about 1 mg/mL or higher (e.g., about 2 mg/mL or higher, about 3 mg/mL or higher, or about 4 mg/mL or higher). Most preferably, the concentration of the conjugate in the inventive composition is about 5 mg/mL. While compositions comprising at least 1 mg/mL of the conjugate are particularly preferred, conjugate concentrations of less than 1 mg/mL (e.g., concentrations of about 0.1 mg/mL to about 0.9 mg/mL) also can be stably maintained in the inventive composition, and thus are within the scope of the invention. Compositions comprising greater than 1 mg/mL of the conjugate molecule are advantageous for clinical and commercial use, in that such concentrations enable single doses of the composition to be prepared in a more convenient (i.e., smaller) volume for administration.

The inventive composition desirably is formulated to be acceptable for pharmaceutical use, such as, for example, administration to a human host in need thereof. To this end, the conjugate molecule preferably is formulated into a composition comprising a physiologically acceptable carrier (e.g., excipient or diluent). Physiologically acceptable carriers are well known and are readily available, and include buffering agents, anti-oxidants, bacteriostats, salts, and solutes that render the formulation isotonic with the blood or other bodily fluid of the human patient, and aqueous and non-aqueous sterile suspensions that can include suspending agents, solubilizers, thickening agents, stabilizers (e.g., surfactants), and preservatives. The choice of carrier will be determined, at least in part, by the location of the target tissue and/or cells, and the particular method used to administer the composition. Examples of suitable carriers and excipients for use in drug conjugate formulations are disclosed in, for example, International (PCT) Patent Application Nos. WO 00/02587, WO 02/060955, and WO 02/092127, and Ghetie et al., *J. Immunol. Methods*, 112, 267-277 (1988). Most preferably, the inventive composition comprises a buffering agent, a surfactant, a tonicifying amount of sodium chloride, and water.

Any suitable pharmaceutically acceptable buffering agent may be used in connection with the inventive composition. Examples of particularly preferred buffering agents include citrate, acetate, succinate, phosphate, and histidine. The inventive composition, however, is not limited to these exemplary buffering agents. The buffering agent may be present in the inventive composition in any suitable concentration, so long as sufficient stability of the composition is achieved under the desired conditions. In this regard, the concentration of the buffering agent in the composition preferably is about 2 mM to about 50 mM (e.g., about 2-10 mM, about 10-20 mM, about 20-30 mM, about 30-40 mM, or about 40-50 mM). Most preferably, the concentration of the buffering agent in the composition is about 5-15 mM (e.g., about 10 mM). The buffering agent desirably is sodium succinate or sodium acetate, but most preferably is sodium citrate. The buffering agent typically is present in the inventive composition such that the pH is maintained within a desired range. In this respect, the inventive composition preferably has a pH of about 5-6 (e.g., about 5, 5.5, or 6). It is believed that compositions with a higher pH (e.g., about pH 6 or higher) are less stable than compositions with a lower pH (i.e., about pH 6 or less). Thus, the inventive composition most preferably has a pH of about 5.5.

In addition to the buffering agent discussed above, the inventive composition also optionally contains a surfactant. Any suitable surfactant can be used in connection with the invention. Suitable surfactants are well known to those skilled in the art. In accordance with the inventive composition, the surfactant desirably is a polysorbate, and preferably is polysorbate 20 or polysorbate 80. Most preferably, the surfactant is polysorbate 20. The surfactant may be present in the inventive composition in any suitable concentration, so long as sufficient stability of the composition is achieved under the desired conditions. In this regard, the concentration of the surfactant in the composition preferably is about 0.002% to about 0.1% wt./vol. (e.g., about 0.002-0.01%, about 0.005-0.02%, or about 0.01-0.1% wt./vol.) of the total volume of the composition. Most preferably, the concentration of the surfactant in the composition is about 0.005-0.02% wt./vol. (e.g., about 0.01% wt./vol.) of the total volume of the composition. Although compositions formulated with surfactants are preferred, compositions formulated without surfactants are also within the scope of the invention.

As an additional stabilizing agent, sodium chloride also is added to the inventive composition. In this regard, the inventive composition comprises a suitable amount, preferably a tonicifying amount, of sodium chloride (NaCl). By the phrase a "tonicifying amount of sodium chloride," it is meant that the concentration of NaCl in the composition is such that the tonicity of the composition is the same as the tonicity of human blood (i.e., isotonic). In this regard, the NaCl can be present in the inventive composition in any suitable concentration, so long as sufficient tonicity and stability is achieved in the inventive composition. Desirably, the concentration of sodium chloride in the composition is about 50 mM to about 500 mM (e.g., about 50-100 mM, about 100-150 mM, about 150-250 mM, about 250-350 mM, or about 350-450 mM). While higher concentrations of sodium chloride (e.g., about 150 mM or more) may render the inventive composition hypertonic rather than isotonic, dilution of such compositions with any suitable isotonic solvent such as, preferably, dextrose 5% in water ("D5W") or normal saline ("NS") prior to human administration would render such compositions only slightly hypertonic and suitable for use in the invention. Preferably, the concentration of sodium chloride in the composition is about 100 mM to about 200 mM (e.g., about 100-140 mM, about 130-170 mM, or about 160-200 mM). Most preferably, the concentration of sodium chloride in the composition is about 110-150 mM (e.g., about 110 mM-130 mM, or about 120 mM).

In a particularly preferred embodiment of the invention, the composition comprises (i) about 5 mg/mL of a conjugate comprising huN901 chemically coupled to DM1, (ii) about 10 mM sodium citrate buffer, (iii) about 0.01% polysorbate 20, (iv) about 120 mM sodium chloride, and (v) water (preferably water suitable for injection (WFI)), wherein the pH of the composition is about 5.5. In another preferred embodiment, the composition comprises (i) about 1 mg/mL or more (e.g., about 1 mg/mL, about 2 mg/mL, 3 mg/mL, about 5 mg/mL, or ranges therebetween) of a conjugate comprising huMy9-6 chemically coupled to DM1, (ii) about 10 mM sodium citrate buffer, (iii) optionally about 0.01% polysorbate 20, (iv) about 135 mM sodium chloride, and (v) water, wherein the pH of the composition is about 5.5. In yet another preferred embodiment, the composition comprises (i) about 1 mg/mL or more (e.g., about 1 mg/mL, about 2 mg/mL, 3 mg/mL, about 5 mg/mL, or ranges therebetween) of a conjugate comprising huMy9-6 chemically coupled to DM4, (ii) about 10 mM sodium citrate buffer, (iii) optionally about 0.01% polysorbate 20, (iv) about 135 mM sodium chloride, and (v) water, wherein the pH of the composition is about 5.5. In an additional preferred embodiment, the composition comprises (i) about 1 mg/mL or more (e.g., about 1 mg/mL, about 2 mg/mL, 3 mg/mL, about 5 mg/mL, or ranges therebetween) of a conjugate comprising huN901 chemically coupled to DM1 via an SMCC linker, (ii) about 10 mM sodium citrate buffer, (iii) optionally about 0.01% polysorbate 20, (iv) about 130 mM sodium chloride, and (v) water, wherein the pH of the composition is about 5.5.

Compositions containing antibodies (or proteins in general) are rendered unstable by oxidation. Thus, in another embodiment of the invention, the composition further comprises an antioxidant. Any suitable antioxidant can be used in the inventive composition. Suitable antioxidants are known in the art and include, for example, superoxide dismutase, glutathione peroxidase, tocotrienols, polyphenols, zinc, manganese, selenium, vitamin C, vitamin E, beta carotene, cysteine, and methionine. The antioxidant used in connection with the inventive composition most preferably is methionine. The antioxidant can be present in the composition in any suitable concentration. Desirably, the concentration of the antioxidant in the composition is about 100 µM to about 100 mM (e.g., about 0.25-1 mM, about 0.5-2 mM, about 5-15 mM, about 20-70 mM, or about 60-90 mM). Most preferably, the concentration of the antioxidant in the composition is about 5-15 mM (e.g., about 10 mM).

In addition to antioxidants, the inventive composition can further be stabilized by the addition of sucrose. The use of sucrose to stabilize antibody formulations is known to those of skill in the art. Any suitable amount of sucrose can be used in the inventive composition, but the concentration of sucrose in the composition desirably is about 0.1% to about 10% wt./vol. (e.g., about 0.1-1%, about 2-5%, or about 7-10% wt./vol.) of the total volume of the composition. Most preferably, the concentration of sucrose in the composition is about 4-6% wt./vol. (e.g., about 5% wt./vol.) of the total volume of the composition.

The invention further provides a packaged composition comprising a sealed container having the inventive composition dispersed therein, and an inert gas overlay. The packaged composition can be overlaid with any suitable inert gas, so long as the inventive composition is stably maintained within the packaged composition. The inert gas preferably is nitrogen or argon. The packaged composition can be presented in unit-dose or multi-dose sealed containers, such as ampules or vials.

In addition to the water-containing composition described herein (also referred to herein as a "liquid" or "aqueous" composition), the invention also provides a lyophilized composition comprising (i) a therapeutically effective amount of a conjugate comprising an antibody chemically coupled to a maytansinoid, (ii) a buffering agent, (iii) a surfactant, (iv) a cryoprotectant, and (v) a bulking agent, wherein the composition has a pH of about 5-6 when reconstituted with water. By "lyophilized" is meant that the composition has been freeze-dried under a vacuum. Lyophilization typically is accomplished by freezing a particular formulation such that the solutes are separated from the solvent(s). The solvent is then removed by sublimation (i.e., primary drying) and next by desorption (i.e., secondary drying). Descriptions of the conjugate (i.e., the antibody chemically coupled to the maytansinoid), buffering agent, surfactant, and components thereof, set forth above in connection with other embodiments of the invention also are applicable to those same aspects of the aforesaid lyophilized composition. Prior to reconstitution of the lyophilized composition, the relative amounts of each component comprising the inventive lyophilized composition can be described in terms of mg of excipient (e.g., buffer, surfactant, bulking agent, cryoprotectant) per mg of conjugate.

While any suitable buffering agent described herein can be used in connection with the inventive lyophilized composition, the inventive lyophilized composition preferably comprises a sodium succinate buffer. The buffering agent can be present in the inventive lyophilized composition in any suitable amount. In particular, the lyophilized composition desirably comprises about 0.1 mg to about 2 mg of the buffering agent per mg of the conjugate (e.g., about 0.1 mg to about 0.5 mg buffering agent per mg of the conjugate, about 0.5 mg to about 1 mg buffering agent per mg of the conjugate, or about 1 mg about 2 mg buffering agent per mg of the conjugate). Most preferably, the lyophilized composition comprises about 0.3 mg sodium succinate buffer per mg of the conjugate.

While any suitable surfactant described herein can be used in connection with the inventive lyophilized composition, the surfactant desirably is a polysorbate, and preferably is polysorbate 20 or polysorbate 80. Most preferably, the surfactant is polysorbate 20. The surfactant may be present in the inventive lyophilized composition in any suitable amount, so long as sufficient stability of the lyophilized composition is achieved under the desired conditions. In this regard, the lyophilized composition desirably comprises about 0.005 mg to about 0.1 mg of the surfactant per mg of the conjugate (e.g., about 0.005 mg to about 0.01 mg surfactant per mg of the conjugate, about 0.01 mg to about 0.05 mg surfactant per mg of the conjugate, or about 0.05 mg to about 0.1 mg surfactant per mg of the conjugate). When the surfactant is polysorbate 20, the lyophilized composition preferably comprises about 0.02 mg polysorbate 20 per mg of the conjugate.

In order to prevent degradation of the active ingredients of the composition during freezing and drying, the inventive lyophilized composition further comprises a cryoprotectant, preferably an amorphous cryoprotectant. The term "cryoprotectant," as used herein, refers to an excipient that protects unstable molecules during freezing. Suitable cryoprotectants for use in the inventive composition are known to those skilled in the art, and include, for example, glycerol, dimethyl sulfoxide (DMSO), polyethylene glycol (PEG), dextran, glucose, trehalose, and sucrose. Most preferably, the cryoprotectant is sucrose. The cryoprotectant may be present in the inventive lyophilized composition in any suitable amount. The lyophilized composition desirably comprises about 0.5 mg to about 5 mg (e.g., about 0.5 mg to about 2 mg) of the cryoprotectant per mg of the conjugate (e.g., about 0.8 mg cryoprotectant per mg of the conjugate, about 2 mg cryoprotectant per mg of the conjugate, or about 4 mg cryoprotectant per mg of the conjugate). When the cryoprotectant is sucrose, the lyophilized composition preferably comprises about 0.5 mg to about 2 mg (e.g., about 1 mg) sucrose per mg of the conjugate.

The inventive lyophilized composition can further contain a bulking agent, preferably a crystallizable bulking agent. Bulking agents typically are used in the art to provide structure and weight to the "cake" produced as a result of lyophilization. Any suitable bulking agent known in the art may be used in connection with the inventive lyophilized composition. Suitable bulking agents include, for example, mannitol, dextran, and glycine. The bulking agent used in the inventive composition most preferably is glycine. The lyophilized composition can contain any suitable amount of the bulking agent, but preferably the lyophilized composition comprises about 2 mg to about 20 mg of the bulking agent per mg of the conjugate (e.g., about 2 mg to about 10 mg bulking agent per mg of the conjugate, about 5 mg to about 10 mg bulking agent per mg of the conjugate, about 10 mg to about 15 mg bulking agent per mg of the conjugate, or about 15 mg to about 20 mg bulking agent per mg of the conjugate). When the bulking agent is glycine, the lyophilized composition preferably comprises about 3.8 mg glycine per mg of the conjugate.

Thus, in accordance with the invention, the contents of a lyophilized composition that is to be reconstituted to contain 5 mg/mL of conjugate (e.g., preferably a conjugate comprising huN901 chemically coupled to DM1) preferably comprises (i) about 0.3 mg sodium succinate buffer per mg of the conjugate, (ii) about 0.02 mg polysorbate 20 per mg of the conjugate, (iii) about 1 mg sucrose per mg of the conjugate, and (iv) about 3.8 mg glycine per mg of the conjugate. Once reconstituted with water, such a lyophilized composition preferably has a pH of about 5.5. Moreover, when the lyophilized composition is reconstituted with water, the descriptions of the relative concentrations of the conjugate, the buffering agent, and the surfactant set forth above in connection with the inventive liquid composition also are applicable to the aforesaid lyophilized composition.

Lyophilization methods are well known in the art and are described in, for example, Wang, W., *Int. J. Pharm.*, 203, 1-60 (2000). For example, the inventive lyophilized composition can be produced using a lyophilization cycle comprising the following steps: (1) pre-cooling at a shelf temperature of 4° C. and ambient chamber pressure for 2.5 hours, (2) freezing at a shelf temperature of −50° C. and ambient chamber pressure for 14 hours, (3) glycine recrystallization at a shelf temperature of −20° C. and ambient chamber pressure for 6 hours, (4) re-freezing at a shelf temperature of −50° C. and ambient chamber pressure for 16 hours, (5) primary drying at a shelf temperature of −13° C. and 100 mTorr of pressure for 24 hours, (6) secondary drying at a shelf temperature of 24° C. and 100 mTorr of pressure for 10 hours, and (7) stopper phase at a shelf temperature of 24° C. and ambient chamber pressure. The inventive lyophilized composition, however, is not limited to compositions produced by the above-described method. Indeed, any suitable lyophilization method can be used to produce the inventive lyophilized composition, and it will be apparent to those skilled in the art that the chosen lyophilization parameters (e.g., drying times) will vary depending on a variety of factors, including the volume of the solution to be lyophilized.

In addition to the preferred embodiments described herein, the inventive composition (whether in liquid or lyophilized form) can comprise additional therapeutic or biologically active agents. For example, therapeutic factors useful in the treatment of a particular indication (e.g., cancer) can be present. Factors that control inflammation, such as ibuprofen or steroids, can be part of the composition to reduce swelling and inflammation associated with in vivo administration of the composition and physiological distress. Immune enhancers can be included in the composition to up regulate the body's natural defenses against disease. Vitamins and minerals, antioxidants, and micronutrients can be co-administered with the composition. Antibiotics, i.e., microbicides and fungicides, can be present to reduce the risk of infection pertaining to the procedures associated with administration of the composition and other disorders.

The invention further provides a method for killing a cell in a human comprising administering to the human a composition comprising (i) a therapeutically effective amount of a conjugate comprising an antibody chemically coupled to a maytansinoid, (ii) a buffering agent, (iii) a surfactant, (iv) a tonicifying amount of sodium chloride, and (v) water, wherein the composition has a pH of about 5-6, such that the antibody binds to the surface of the cell and the cytotoxicity of the maytansinoid is activated, whereby the cell is killed. Descriptions of the conjugate (i.e., the antibody chemically coupled to the maytansinoid), excipients (e.g., buffering agent, surfactant, sodium chloride, etc.), and components thereof, set forth above in connection with other embodiments of the invention also are applicable to those same aspects of the aforesaid inventive method.

The inventive method involves administering the inventive composition to a human. Ideally, the inventive method is used to target and kill cells affected by a disease, particularly a disease associated with elevated levels of cellular proliferation, such as cancer. Thus, in this regard, the inventive method preferably is used to kill tumor cells in a human, thereby resulting in the prevention, amelioration, and/or cure of the cancer.

While any suitable means of administering the composition to a human can be used within the context of the invention, typically and preferably the inventive composition is administered to a human via injection, and most preferably via infusion. By the term "injection," it is meant that the composition is forcefully introduced into a target tissue of the human. By the term "infusion," it is meant that the composition is introduced into a tissue, typically and preferably a vein, of the human. The composition can be administered to the human by any suitable route, but preferably is administered to the human intravenously or intraperitoneally. When the inventive method is employed to kill tumor cells, however, intratumoral administration of the inventive composition is particularly preferred. When the inventive composition is administered by injecting, any suitable injection device can be used to administer the composition directly to a tumor. For example, the common medical syringe can be used to directly inject the composition into a subcutaneous tumor. Alternatively, the composition can be topically applied to the tumor by bathing the tumor in the inventive liquid composition. Likewise, the tumor can be perfused with the inventive composition over a period of time using any suitable delivery device, e.g., a catheter. While less preferred, other routes of administration can be used to deliver the composition to the human. Indeed, although more than one route can be used to administer the inventive composition, a particular route can provide a more immediate and more effective reaction than another route. For example, while not particularly preferred, the inventive composition can be applied or instilled into body cavities, absorbed through the skin, inhaled, or administered parenterally via, for instance, intramuscular or intraarterial administration. Preferably, the inventive composition parenterally administered to a human is specifically targeted to particular cells, e.g., cancer cells.

As described herein, the conjugate comprises an antibody, which is preferably a humanized monoclonal antibody, such as huN901, huMy9-6, huB4, or huC242. Other suitable antibodies include, for example, trastuzumab, bivatuzumab, sibrotuzumab, and rituximab. When compositions comprising such conjugates are employed in the inventive method, the antibody targets the conjugate to a desired cell (e.g., a tumor cell) through interactions with antigens (e.g., tumor-specific antigens) expressed at the surface of the cell (e.g., tumor cell). Tumor-specific antigens have been extensively described in the prior art for a variety of tumors, including, for example, epithelial cancers (e.g., MUC1), and breast and ovarian cancer (e.g., HER2/neu), (see, e.g., Bartnes, *Tidsskr. Nor. Laegeforen.*, 121, 2941-5 (2001), and von Mensdorff-Pouilly et al., *Int. J. Biol. Markers*, 15, 343-356 (2000)).

In a preferred embodiment of the invention, the antibody (e.g., huMy9-6) binds to the CD33 antigen, which is expressed, for example, by acute myeloid leukemia cells. In another preferred embodiment, the antibody (e.g., huB4) binds to the CD19 antigen, which is expressed, for example, by human B-cell lymphoma cells. Alternatively, the antibody (e.g., huC242) binds to the CanAg antigen, which is expressed by a number of cancer cell types, including, for example, colorectal, pancreatic, gastric, and other gastrointestinal cancers, and the majority of non-small-cell lung cancers. Most preferably, the antibody (e.g., huN901) binds to the NCAM/CD56 antigen, which is expressed, for example, by small cell lung carcinoma (SCLC) cells, and by other cancers of neuroendocrine origin. Other preferred antigens to which the antibody can bind include the $GD_3$ antigen, PSMA, the alpha-folate receptor, Her2/neu, CD44v6, the fetoacinar pancreatic (FAP) antigen, the Cripto-1 antigen, the CA6 antigen, CD20, CA 55.1, MN/CA IX, and chondroitin sulfate proteoglycan (see, e.g., Chang et al., *Cancer Res.*, 59, 3192-98 (1999), Miotti et al., *Int. J. Cancer*, 39, 297-303, (1987), Colomer et al., supra, Heider et al., supra, Welt et al., supra, LePage et al., *American Assn. For Cancer Research (AACR)*, 2003 Anuual Meeting, Poster Abstact No. 749, Kearse et al., *Int. J. Cancer*, 88, 866-72 (2000), Maloney et al., supra, Opavsky et al., *Genomics*, 33, 480-87 (1996), Behm et al., *Blood*, 87, 1134-39 (1996), and U.S. Pat. No. 5,665,357). Upon binding of the conjugate to a target (i.e., tumor) cell via any of the tumor specific antigens or receptors described herein, the cytotoxicity of the maytansinoid is activated. Examples of mechanisms by which maytansinoid cytotoxicity can be activated include release of the free maytansinoid inside the cell via cleavage of the disulfide linkage between the antibody and the maytansinoid, antibody degradation within the cell, and activation of maytansinoid cytotoxicity at the cell surface. The inventive method, however, is not limited to these exemplary modes of maytansinoid activation. Indeed, any mechanism that activates the cytotoxicity of the maytansinoid is within the scope of the inventive method.

For the purposes of human administration, the inventive liquid composition described herein may be administered (e.g., infused) directly to a human, or diluted with a suitable diluent immediately prior to administration. Suitable diluents are known in the art and include D5W and normal saline (NS). Dilutions of 1:1, 1:2, 1:3, or more (e.g., 1:5, 1:10, or even 1:50) with suitable diluents are possible. Dilution of the inventive composition desirably does not reduce the concentration of the conjugate molecule in the composition below about 0.1 mg/mL. Upon diluting the inventive liquid composition, the previously described concentrations of each of the components (e.g., buffering agent, surfactant, and sodium chloride) of the composition are correspondingly reduced.

When the inventive lyophilized composition described herein is administered to a human, the composition must be first reconstituted by adding a sterile liquid excipient, for example, water suitable for injection, D5W, or NS, immediately prior to use. Thus, the invention further provides a method for killing a cell in a human comprising (a) providing the lyophilized composition as described herein, (b) adding water to the lyophilized composition to provide a reconstituted composition, and (c) administering the reconstituted composition to the human such that the antibody binds to the surface of the cell and the maytansinoid is internalized by the cell, whereby the cell is killed. Descriptions of the lyophilized composition, administration routes, tumor specific antigens, and components thereof, set forth above in connection with other embodiments of the invention also are applicable to those same aspects of the aforesaid inventive method. Moreover, as discussed herein, after the inventive lyophilized composition is reconstituted with water, the descriptions of the relative concentrations of the conjugate and excipients (e.g., buffering agent, surfactant, cryoprotectant, and bulking agent) described above in connection with the inventive liquid composition also are applicable to those same aspects of the aforesaid inventive method.

As discussed herein, the inventive method, whether employing a liquid composition or a lyophilized composition, preferably is used in connection with treating cancer. The inventive method can be used to treat cancer of any type, including, for example, cancer of the lung, breast, colon, prostate, kidney, pancreas, ovary, blood, and lymphatic organs. While less preferred, the inventive composition may be used to treat other diseases associated with cellular proliferation including autoimmune diseases (e.g., systemic lupus, rheumatoid arthritis, and multiple sclerosis), graft rejections (e.g., renal transplant rejection, liver transplant rejection, lung transplant rejection, cardiac transplant rejection, and bone marrow transplant rejection), graft versus host disease, viral infections (e.g., CMV infection, HIV infection, AIDS, etc,), and parasitic infections (e.g., giardiasis, amoebiasis, schistosomiasis), and others.

The following examples further illustrate the invention but, of course, should not be construed as in any way limiting its scope.

EXAMPLE 1

This example demonstrates the production of a composition comprising a conjugate comprising an antibody chemically coupled to a maytansinoid, buffering agent, surfactant, tonicifying amount of sodium chloride, and water.

The generation of a conjugate comprising the huN901 monoclonal antibody chemically coupled to the maytansinoid DM1 via disulfide bonds ("huN901:DM1") has been previously described (see, e.g., U.S. Pat. No. 6,441,163). Formulations containing either 1 mg/mL or 5 mg/mL of the huN901:DM1 conjugate in the presence of each of the above-described excipients individually were prepared. The stability of each of the formulations was assessed using the following assays: visual inspection to detect particulates, a chromatographic method to measure free drug-related species, and HPLC size exclusion chromatography (SEC-HPLC) to detect high and low molecular weight conjugate-related species. With respect to visual inspection, the presence of particulates are indicative of instability and, therefore, are considered undesirable, while a clear solution is indicative of a stable formulation. The chromatographic assay was used to measure the amount of free drug at 4° C. and 25° C. The results of each of these assays suggested that a formulation containing about 5 mg/mL huN901:DM1 conjugate, about 10 mM sodium citrate, about 0.01% polysorbate and sodium chloride at pH 5.5 (i.e., the inventive liquid composition) would have superior stability.

To confirm the stability of the above-described formulation with respect to dimer formation, which also is an indicator of instability, the huN901:DM1 conjugate was concentrated and formulated in either phosphate buffered saline (PBS), pH 6.5 (Formulations 1A-1C), or 10 mM sodium citrate, 0.01% polysorbate 20, 60 mM NaCl, pH 5.5 (Formulation 1D). After 6 months at 4° C. or 25° C. the samples were assayed by SEC-HPLC. The results of this analysis are set forth in Table 1.

the visual inspection assay, the chromatographic assay, and the SEC-HPLC assay indicate that the inventive composition was the most stable of the tested formulations.

EXAMPLE 2

This example demonstrates the production of a composition comprising a conjugate comprising an antibody chemically coupled to a maytansinoid, buffering agent, surfactant or sucrose, tonicifying amount of sodium chloride, and water A conjugate comprising the huN901 monoclonal antibody chemically coupled to the maytansinoid DM1 via an N-succinimidyl 4-(2-pyridyldithio)pentanoate (SPP) linker ("huN901-SPP-DM1") was prepared using methods described herein and known in the art (see, e.g., U.S. Pat. No. 6,441,163). The huN901-SPP-DM1 conjugate was formulated in either (a) PBS, pH 6.5 (Formulations 2A and 2B) or (b) 10 mM sodium citrate, 0.01% polysorbate 20, 135 mM NaCl, pH 5.5 (Formulation 2C) at varying concentrations. Samples of each of the formulations were incubated at 4° C. and 25° C. for 6 months, after which the formulations were

TABLE 1

| Formulation | Conjugate Concentration (mg/mL) | Buffering Agent | Surfactant | NaCl | % Conjugate Dimer after 6 months at 4° C. | 25° C. |
|---|---|---|---|---|---|---|
| 1A (comparative) | 5.0 | PBS, pH 6.5 | None | None | 5.5 | 9.3 |
| 1B (comparative) | 3.8 | PBS, pH 6.5 | None | None | 5.5 | 8.4 |
| 1C (comparative) | 1.2 | PBS, pH 6.5 | None | None | 4.9 | 6.0 |
| 1D (invention) | 5.0 | Sodium citrate, pH 5.5 | 0.01% polysorbate 20 | 60 mM | 5.1 | 6.0 |

These results demonstrate that compositions of the invention (as represented by Formulation 1D) protected against formation of conjugate dimer. Thus, the combined results of tested for the presence of free drug and conjugate dimers by chromatographic assays. The results of these analyses are set forth in Table 2.

TABLE 2

| | Conjugate Concentration | | | % Dimer | | | % Free Drug | | |
|---|---|---|---|---|---|---|---|---|---|
| | | | | Time | 6 months | | Time | 6 months | |
| Formulation | (mg/mL) | Buffering Agent | Surfactant | Zero | 4° C. | 25° C. | Zero | 4° C. | 25° C. |
| 2A (Comparative) | 1.0 | PBS, pH 6.5 | None | 4.8 | 5.8 | 6.1 | 1.1 | 1.6 | 4.6 |
| 2B (Comparative) | 5.0 | PBS, pH 6.5 | None | 5.2 | 8.5 | 10.1 | 1.1 | 1.6 | 4.9 |
| 2C (Invention) | 5.0 | Sodium citrate, pH 5.5 | 0.01% polysorbate | 4.4 | 5.5 | 6.4 | 0.4 | 1.2 | 2.9 |

In addition to the results recited in Table 2, the formulations were visually inspected for particulates. The inventive formulation (Formulation 2C) was visually clear after 6 months' storage at 4° C., while particulates and sediments were observed in the comparative formulations (as represented by formulations 2A and 2B).

These results demonstrate the enhanced stability of compositions of the invention.

EXAMPLE 3

This example demonstrates the production of a composition comprising a conjugate comprising an antibody chemically coupled to a maytansinoid, buffering agent, surfactant, tonicifying amount of sodium chloride, an antioxidant, and water.

A conjugate comprising the huN901 monoclonal antibody chemically coupled to the maytansinoid DM1 via an N-succinimidyl 4-(N-maleimidomethyl)cyclohexane-1-carboxylate (SMCC) linker ("huN901-SMCC-DM1") was prepared using methods described herein and known in the art (see, e.g., U.S. Pat. No. 6,441,163). 1 mg/mL huN901-SMCC-DM1 conjugate was formulated in either (a) phosphate buffered saline (PBS), pH 6.5 (Formulation 3A), (b) 10 mM sodium citrate, 0.01% polysorbate 20, 130 mM NaCl, pH 5.5 (Formulation 3B), or (c) 10 mM sodium citrate, 0.01% polysorbate 20, 130 mM NaCl, 10 mM methionine, pH 5.5 (Formulation 3C). After a 3.5-month incubation at 25° C. and 37° C., samples of each of the formulations were tested for the presence of conjugate dimers by a chromatographic assay. The results of this analysis are set forth in Table 3.

TABLE 3

| | | | | | % Dimer | |
| --- | --- | --- | --- | --- | --- | --- |
| | | | | Time | 3.5-months | |
| Formulation | Buffering Agent | Surfactant | Antioxidant | Zero | 25° C. | 37° C. |
| 3A (comparative) | PBS, pH 6.5 | None | None | 4.0 | 5.8 | 11.2 |
| 3B (invention) | Sodium citrate, pH 5.5 | 0.01% polysorbate 20 | None | 4.0 | 4.7 | 6.3 |
| 3C (invention) | Sodium citrate, pH 5.5 | 0.01% polysorbate 20 | 10 mM methionine | 4.0 | 4.4 | 4.8 |

These results demonstrate that compositions of the invention (as represented by Formulations 3B and 3C) provide enhanced stability.

EXAMPLE 4

This example demonstrates the production of a composition comprising a conjugate comprising the monoclonal antibody huMy9-6 chemically coupled to the maytansinoid DM1, buffering agent, tonicifying amount of sodium chloride, and water, with or without a surfactant and sucrose.

A conjugate comprising the huMy9-6 monoclonal antibody chemically coupled to the maytansinoid DM1 via an N-succinimidyl 4-(2-pyridyldithio)pentanoate (SPP) linker ("huMy9-6-SPP-DM1") was prepared using methods described herein and known in the art (see, e.g., U.S. Pat. No. 6,441,163). 1 mg/mL of the huMy9-6-SPP-DM1 conjugate was formulated in either (a) phosphate buffered saline (PBS), pH 6.5 (Formulation 4A), (b) 10 mM sodium citrate, 135 mM NaCl, pH 5.5 (Formulation 4B), (c) 10 mM sodium citrate, 0.01% polysorbate 20, 135 mM NaCl, pH 5.5 (Formulation 4C), or (d) 10 mM sodium citrate, 5% sucrose, 60 mM NaCl, pH 5.5 (Formulation 4D). After a three-month incubation at 4° C. or 25° C., samples of each of the formulations were assayed by SEC-HPLC to measure high molecular weight (HMW) species, and by a chromatographic assay to measure free drug species. The results of this analysis are set forth in Table 4.

TABLE 4

| | | | | | | % Free Drug | | % HMW Species | | |
| --- | --- | --- | --- | --- | --- | --- | --- | --- | --- | --- |
| | | | | | Time | 3 months | | Time | 3 months | |
| Formulation | Buffering Agent | NaCl (mM) | Surfactant | Stabilizer | Zero | 4° C. | 25° C. | Zero | 4° C. | 25° C. |
| 4A (comparative) | PBS, pH 6.5 | None | None | None | 0.2 | 1.3 | 3.2 | 0.5 | 1.4 | 2.0 |

TABLE 4-continued

| | | | | | % Free Drug | | | % HMW Species | | |
|---|---|---|---|---|---|---|---|---|---|---|
| | | NaCl | | | Time | 3 months | | Time | 3 months | |
| Formulation | Buffering Agent | (mM) | Surfactant | Stabilizer | Zero | 4° C. | 25° C. | Zero | 4° C. | 25° C. |
| 4B (invention) | Sodium citrate, pH 5.5 | 135 | None | None | 0.1 | 1.0 | 1.8 | 0.4 | 0.7 | 1.4 |
| 4C (invention) | Sodium citrate, pH 5.5 | 135 | 0.01% polysorbate 20 | None | 0.1 | 1.0 | 1.8 | 0.5 | 0.8 | 1.8 |
| 4D (invention) | Sodium citrate, pH 5.5 | 60 | None | 5% sucrose | 0.1 | 1.1 | 1.9 | 0.4 | 0.5 | 0.8 |

In addition, samples of Formulations 4A and 4B were incubated at 4° C. and 25° C. for three months, and then tested for conjugate dimer formation as discussed above. The results of this analysis are set forth in Table 5.

TABLE 5

| | | % Dimer | | |
|---|---|---|---|---|
| | | | 3 months | |
| Formulation | Buffering Agent | Time Zero | 4° C. | 25° C. |
| 4A (comparative) | PBS, pH 6.5 | 6.3 | 10.8 | 12.3 |
| 4B (invention) | Sodium citrate, pH 5.5 | 5.7 | 7.0 | 7.7 |

These results demonstrate that compositions of the invention (as represented by Formulations 4B, 4C, and 4D) provide enhanced stability, and that sucrose adds additional stabilizing benefits.

EXAMPLE 5

This example demonstrates the production of a composition comprising a conjugate comprising the monoclonal antibody huMy9-6 chemically coupled to the maytansinoid DM4, buffering agent, tonicifying amount of sodium chloride, and water, with or without a surfactant.

A conjugate comprising the huMy9-6 monoclonal antibody chemically coupled to the maytansinoid DM4 via an N-succinimidyl 4-(2-pyridyldithio)butanoate (SPDB) linker ("huMy9-6-SPDB-DM4") was prepared using methods described herein and known in the art (see, e.g., U.S. Pat. No. 6,441,163). 1 mg/mL of the huMy9-6-SPDB-DM4 conjugate was formulated in either (a) phosphate buffered saline (PBS), pH 6.5, (b) 10 mM sodium citrate, 135 mM NaCl, pH 5.5, or (c) 10 mM sodium citrate, 0.01% polysorbate 20, 135 mM NaCl, pH 5.5. To confirm the stability of the above-described formulations, samples of each of the formulations were tested for the presence of particles using a HIAC particle counter after a six-month incubation at −80° C. Samples of each of the formulations also were tested for the presence of free drug species as described above after a six-month incubation at 4° C. or 25° C. The results of these analyses are set forth in Table 6.

TABLE 6

| | | | NaCl | >5 μm Particles after 6 months | % Free Drug after 6 months | |
|---|---|---|---|---|---|---|
| Formulation | Buffering Agent | Surfactant | mM | at −80° C. | 4° C. | 25° C. |
| 5A (comparative) | PBS, pH 6.5 | None | None | 21218 | 1.6 | 5.0 |
| 5B (invention) | Sodium citrate, pH 5.5 | None | 135 | 8778 | 1.2 | 2.5 |
| 5C (invention) | Sodium citrate, pH 5.5 | 0.01% polysorbate 20 | 135 | 776 | 1.1 | 2.8 |

These results demonstrate that the compositions of the invention (as represented by Formulations 5B and 5C) protected against the formation of free drug species and particulates, and that the presence of polysorbate added additional stability protection against particle formation.

EXAMPLE 6

This example demonstrates the production of a lyophilized composition comprising a conjugate comprising the monoclonal antibody huN901 chemically coupled to the maytansinoid DM1.

The generation of a conjugate comprising the huN901 human monoclonal antibody chemically coupled to the maytansinoid DM1 via disulfide bonds ("huN901:DM1") has been previously described (see, e.g., U.S. Pat. No. 6,441,163). Four formulations, designated Formulations 6A-6D, were prepared. Each formulation contained (a) 1 mg/mL huN901-DM1, (b) either 10 mM sodium citrate or 10 mM sodium succinate, (c) 0.5% wt./vol. sucrose, (d) 250 mM glycine, and (e) water, with or without 0.01% wt./vol. polysorbate 20, at a pH of 5.5, as set forth in Table 7.

TABLE 7

| Formulation | Buffering Agent | Surfactant | Cryoprotectant | Bulking Agent |
|---|---|---|---|---|
| 6A (comparative) | sodium citrate | none | sucrose | glycine |
| 6B (comparative) | sodium citrate | polysorbate 20 | sucrose | glycine |
| 6C (comparative) | sodium succinate | none | sucrose | glycine |
| 6D (invention) | sodium succinate | polysorbate 20 | sucrose | glycine |

1 mL samples of each of the Formulations 6A-6D were lyophilized in 1 mL vials according to the lyophilization scheme recited in Table 8.

TABLE 8

| Lyophilization Step | Shelf Temp (° C.) | Chamber Pressure (mTorr) | Step Duration (hours) |
|---|---|---|---|
| Pre-cool | 4 | Ambient | 2.5 |
| Freeze | −50 | Ambient | 14 |
| Glycine recrystallization | −20 | Ambient | 6 |
| Re-freeze | −50 | Ambient | 16 |
| Primary dry | −13 | 100 | 24 |
| Secondary dry | 24 | 100 | 10 |
| Stopper | 24 | Ambient | — |

After lyophilization, samples of each of Formulations 6A-6D displayed solid, uniform white cakes, and samples of all formulations resuspended rapidly (i.e., less than 20 seconds for complete dissolution) when reconstituted in distilled water. The reconstituted samples were analyzed for visual appearance and high molecular weight species by HPLC size exclusion chromatography (SEC-HPLC). The presence of particulates and/or a high molecular weight species are indicative of instability and, therefore, are considered undesirable, while a clear solution is indicative of a stable formulation. The results of this analysis are set forth in Table 9.

TABLE 9

| | Post-reconstitution | |
|---|---|---|
| Formulation | Appearance | High Molecular Weight (%) |
| 6A (comparative) | Opalescent, particles | 0.3 |
| 6B (comparative) | Particles | 0 |
| 6C (comparative) | Clear, no particulates | 0.39 |
| 6D (invention) | Clear, no particulates | 0.05 |

Based on these results, the lyophilized composition of the invention (i.e., Formulation 6D) was the only composition that effectively prevented the formation of particulates and high molecular weight species upon lyophilization. The inventive lyophilized composition was the most stable of the tested formulations.

EXAMPLE 7

This example demonstrates the stability of a lyophilized composition comprising a conjugate comprising the monoclonal antibody huN901 chemically coupled to the maytansinoid DM1.

A conjugate comprising the huN901 monoclonal antibody chemically coupled to the maytansinoid DM1 via an N-succinimidyl 4-(2-pyridyldithio)pentanoate (SPP) linker ("huN901-SPP-DM1") was prepared as described herein. 5 mg/mL of the huN901-SPP-DM1 conjugate was formulated in either (a) PBS, pH 6.5 and stored as a liquid or (b) 10 mM sodium succinate, 0.5% sucrose, 0.01% polysorbate 20, 250 mM glycine, pH 5.5, and lyophilized as described in Example 6. Samples were incubated at 4° C. and 25° C. for 6 months, after which they were tested for the presence of particles, conjugate dimers, and free drug species as described herein. The results of these analyses are set forth in Table 10.

TABLE 10

| | Appearance | | | Particles | % Dimer | | | % Free Drug | | |
|---|---|---|---|---|---|---|---|---|---|---|
| | | 6 month | | (>5 μm) | Time | 6 months | | Time | 6 months | |
| Formulation | Time 0 | 4° C. | 25° C. | 25° C. | Zero | 4° C. | 25° C. | Zero | 4° C. | 25° C. |
| 7A liquid (Comparative) | clear | particulates and sediments | clear | 1122 | 5.2 | 8.5 | 10.1 | 1.1 | 1.6 | 4.9 |
| 7B lyophilized | White solid cake; 20-sec | White solid cake; 19-sec | White solid cake; 15-sec | 24 | 3.8 | 4.1 | 4.6 | 0.6 | 0.6 | 0.9 |

TABLE 10-continued

| | | Appearance | | Particles | % Dimer | | | % Free Drug | | |
|---|---|---|---|---|---|---|---|---|---|---|
| | | 6 month | | (>5 µm) | Time | 6 months | | Time | 6 months | |
| Formulation | Time 0 | 4° C. | 25° C. | 25° C. | Zero | 4° C. | 25° C. | Zero | 4° C. | 25° C. |
| (Invention) | reconstitution time, clear solution, no particulate | reconstitution time, clear solution, no particulate | reconstitution time, clear solution, no particulate | | | | | | | |

These results demonstrate the stability of the inventive lyophilized composition, as evidenced by the reduction in particles, conjugate dimer, and free drug as compared to the liquid compositions formulated in PBS.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A composition comprising (i) about 0.1 mg/mL to about 5 mg/mL of a conjugate comprising humanized antibody huC242 that binds to CANAG wherein the antibody is chemically coupled to a maytansinoid that is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)-maytansine (DM4), (ii) about 2 mM to about 50 mM of a buffering agent selected from the group consisting of sodium citrate, sodium acetate, and sodium succinate, (iii) polysorbate 20 or polysorbate 80 that is about 0.002% to about 0.1% of the total volume of the composition, (iv) about 50 mM to about 500 mM sodium chloride, and (v) water, wherein the composition has a pH of about 5-6.

2. The composition of claim 1, wherein the maytansinoid is DM1.

3. The composition of claim 1, wherein the maytansinoid is DM4.

4. The composition of claim 1, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

5. The composition of claim 1, wherein the concentration of the conjugate in the composition is about 5 mg/mL.

6. The composition of claim 1, wherein the composition comprises about 10 mM sodium citrate, and the pH of the composition is about 5.5.

7. The composition of claim 1, wherein the composition comprises polysorbate 20.

8. The composition of claim 7, wherein the concentration of polysorbate 20 in the composition is about 0.0 1% of the total volume of the composition.

9. The composition of claim 1, wherein the concentration of sodium chloride in the composition is about 100 mM to about 200 mM.

10. The composition of claim 9, wherein the concentration of sodium chloride in the composition is about 120 mM.

11. The composition of claim 1, wherein the composition further comprises an antioxidant.

12. The composition of claim 11, wherein the concentration of the antioxidant in the composition is about 100 µM to about 100 mM.

13. The composition of claim 12, wherein the antioxidant is selected from the group consisting of superoxide dismutase, glutathione peroxidase, tocotrienols, polyphenols, zinc, manganese, selenium, vitamin C, vitamin E, beta carotene, cysteine, and methionine.

14. The composition of claim 13, wherein the antioxidant is methionine.

15. The composition of claim 14, wherein the concentration of methionine in the composition is about 10 mM.

16. The composition of claim 1, wherein the composition further comprises sucrose.

17. The composition of claim 16, wherein the concentration of sucrose in the composition is about 0.1% to about 10% of the total volume of the composition.

18. The composition of claim 17, wherein the concentration of sucrose in the composition is about 5% of the total volume of the composition.

19. A packaged composition comprising a sealed container and dispersed therein the composition of claim 1 and an inert gas overlay.

20. The packaged composition of claim 19, wherein the inert gas is nitrogen or argon.

21. A method for killing a cell in a human comprising administering to the human a composition comprising (i) about 0.1 mg/mL to about 5 mg/mL of a conjugate comprising humanized antibody huC242 that binds to CANAG wherein the antibody is chemically coupled to a maytansinoid that is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)-maytansine (DM4), (ii) about 2 mM to about 50 mM of a buffering agent selected from the group consisting of sodium citrate, sodium acetate, and sodium succinate, (iii) polysorbate 9 or polysorbate 80 that is about 0.002% to about 0.1% of the total volume of the composition, (iv) about 50 mM to about 500 mM sodium chloride, and (v) water, wherein the composition has a pH of about 5-6, such that the antibody binds to CANAG present on the surface of the cell and the cytotoxicity of the maytansinoid is activated, whereby the cell is killed.

22. The method of claim 21, wherein the cell is a tumor cell.

23. The method of claim 21, wherein the maytansinoid is DM1.

24. The method of claim 21, wherein the maytansinoid is DM4.

25. The method of claim 21, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

26. The method of claim 21, wherein the concentration of the conjugate in the composition is about 5 mg/mL.

27. The method of claim 21, wherein the composition comprises polysorbate 20.

28. The method of claim 21, wherein the composition further comprises an antioxidant.

29. The method of claim 28, wherein the antioxidant is selected from the group consisting of superoxide dismutase, glutathione peroxidase, tocotrienols, polyphenols, zinc, manganese, selenium, vitamin C, vitamin B, beta carotene, cysteine, and methionine.

30. The method of claim 29, wherein the antioxidant is methionine.

31. The method of claim 21, wherein the composition further comprises sucrose.

32. The method of claim 21, wherein the composition is administered to the human intravenously, intraperitoneally, or intratumorally.

33. A lyophilized composition comprising (i) a therapeutically effective amount of a conjugate comprising humanized antibody huC242 that binds to CANAG wherein the antibody is chemically coupled to a maytansinoid that is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)-maytansine (DM4), (ii) about 0.1 mg to about 2 mg of a buffering agent selected from the group consisting of sodium citrate, sodium acetate, and sodium succinate per mg of the conjugate, (iii) about 0.005 mg to about 0.1 mg of polysorbate 20 or polysorbate 80 per mg of the conjugate, (iv) about 0.5 mg to about 5 mg of sucrose per mg of the conjugate, and (v) about 2 mg to about 20 mg of glycine per mg of the conjugate, wherein the composition has a pH of about 5-6 when reconstituted with water.

34. The lyophilized composition of claim 33, wherein the maytansinoid is DM1.

35. The lyophilized composition of claim 33, wherein the maytansinoid is DM4.

36. The lyophilized composition of claim 33, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

37. The lyophilized composition of claim 33, wherein the composition comprises about 0.3 mg sodium succinate per mg of the conjugate.

38. The lyophilized composition of claim 33, wherein the composition comprises polysorbate 20.

39. The lyophilized composition of claim 38, wherein the composition comprises about 0.02 mg polysorbate 20 per mg of the conjugate.

40. The lyophilized composition of claim 33, wherein the composition comprises about 1 mg sucrose per mg of the conjugate.

41. The lyophilized composition of claim 33, wherein the composition comprises about 3.8 mg glycine per mg of the conjugate.

42. A method for killing a cell in a human comprising (a) providing the lyophilized composition of claim 33, (b) adding water to the lyophilized composition to provide a reconstituted composition, and (c) administering the reconstituted composition to the human such that the antibody binds to CANAG present on the surface of the cell and the cytotoxicity of the maytansinoid is activated, whereby the cell is killed.

43. The method of claim 42, wherein the cell is a tumor cell.

44. The method of claim 42, wherein the maytansinoid is DM1.

45. The method of claim 42, wherein the maytansinoid is DM4.

46. The method of claim 42, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

47. The method of claim 42, wherein the concentration of the conjugate in the reconstituted composition is about 0.1 mg/mL to about 5 mg/mL.

48. The method of claim 47, wherein the concentration of the conjugate in the reconstituted composition is about 1 mg/mL.

49. The method of claim 47, wherein the concentration of the conjugate in the reconstituted composition is about 5 mg/mL.

50. The method of claim 42, wherein the concentration of the buffering agent in the reconstituted composition is about 2 mM to about 50 mM.

51. The method of claim 50, wherein the reconstituted composition comprises 10 mM sodium succinate, and the pH of the reconstituted composition is about 5.5.

52. The method of claim 42, wherein the concentration of polysorbate 20 or polysorbate 80 in the reconstituted composition is about 0.002% to about 0.1% of the total volume of the reconstituted composition.

53. The method of claim 52, wherein the reconstituted composition comprises polysorbate 20.

54. The method of claim 53, wherein the concentration of polysorbate 20 in the reconstituted composition is about 0.0 1% of the total volume of the reconstituted composition.

55. The method of claim 42, wherein the concentration of sucrose in the reconstituted composition is about 0.1% to about 3% of the total volume of the reconstituted composition.

56. The method of claim 55, wherein the concentration of sucrose in the reconstituted composition is about 0.5% of the total volume of the reconstituted composition.

57. The method of claim 42, wherein the concentration of glycine in the reconstituted composition is about 50 mM to about 500 mM.

58. The method of claim 57, wherein the concentration of glycine in the reconstituted composition is about 250 mM.

59. The method of claim 42, wherein the reconstituted composition is administered to the human intravenously, intraperitoneally, or intratumorally.

60. A lyophilized composition comprising (i) a therapeutically effective amount of a conjugate comprising humanized antibody huC242 that binds to CANAG wherein the antibody is chemically coupled to a maytansinoid that is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)-maytansine (DM4), (ii) about 0.1 mg to about 2 mg of a buffering agent selected from the group consisting of sodium citrate, sodium acetate, and sodium succinate per mg of the conjugate, (iii) about 0.5 mg to about 5 mg of sucrose per mg of the conjugate, and (iv) about 2 mg to about 20 mg of glycine per mg of the conjugate, wherein the composition has a pH of about 5-6 when reconstituted with water.

61. The composition of claim 1, wherein the composition comprises (i) about 5 mg/mL of a conjugate comprising huC242 that binds to CANAG wherein the antibody is chemically coupled to DM1, (ii) about 10 mM sodium citrate, (iii) about 0.01% polysorbate 20, (iv) about 120 mM sodium chloride, and (v) water, wherein the pH of the composition is about 5.5.

62. The composition of claim 1, wherein the composition comprises (i) about 0.1 mg/mL to about 5 mg/mL of a conjugate comprising humanized antibody huC242 that binds to CANAG wherein the antibody is chemically coupled to DM1 (ii) about 10 mM of a buffering agent selected from the group consisting of sodium citrate, sodium acetate, and sodium succinate, (iii) polysorbate 20 or polysorbate 80 that is about 0.0 1% of the total volume of the composition, (iv) about 120 mM sodium chloride, and (v) water, wherein the composition has a pH of about 5.5.

63. The composition of claim 1, wherein the composition comprises (i) about 0.1 mg/mL to about 5 mg/mL of a conjugate comprising humanized antibody huC242 that binds to CANAG wherein the antibody is chemically coupled to DM4 (ii) about 10 mM of a buffering agent selected from the group consisting of sodium citrate, sodium acetate, and sodium succinate, (iii) polysorbate 20 or polysorbate 80 that is about 0.0 1% of the total volume of the composition, (iv) about 120 mM sodium chloride, and (v) water, wherein the composition has a pH of about 5.5.

64. The method of claim 21, wherein the composition comprises (i) 0.1 mg/mL to about 5 mg/mL of a conjugate comprising humanized antibody huC242 that binds to CANAG wherein the antibody is chemically coupled to DM1 (ii) about 10 mM of a buffering agent selected from the group consisting of sodium citrate, sodium acetate, and sodium succinate, (iii) polysorbate 20 or polysorbate 80 that is about 0.0 1% of the total volume of the composition, (iv) about 120 mM sodium chloride, and (v) water, wherein the composition has a pH of about 5.5.

65. The method of claim 21, wherein the composition comprises (i) about 0.1 mg/mL mg/mL to about 5 mg/mL of a conjugate comprising humanized antibody huC242 that binds to CANAG wherein the antibody is chemically coupled to DM4 (ii) about 10 mM of a buffering agent selected from the group consisting of sodium citrate, sodium acetate, and sodium succinate, (iii) polysorbate 20 or polysorbate 80 that is about 0.0 1% of the total volume of the composition, (iv) about 120 mM sodium chloride, and (v) water, wherein the composition has a pH of about 5.5.

66. The lyophilized composition of claim 33, wherein the composition comprises (i) a therapeutically effective amount of a conjugate comprising humanized antibody huC242 that binds to CANAG wherein the antibody is chemically coupled to DM1 (ii) about 0.3 mg a buffering agent selected from the group consisting of sodium citrate, sodium acetate, and sodium succinate per mg of the conjugate, (iii) about 0.02 mg of polysorbate 20 or polysorbate 80 per mg of the conjugate, (iv) about 1 mg of sucrose per mg of the conjugate, and (v) about 3.8 mg of glycine per mg of the conjugate, wherein the composition has a pH of about 5.5 when reconstituted with water.

67. A method for killing a cell in a human comprising (a) providing the lyophilized composition of claim 66, (b) adding water to the lyophilized composition to provide a reconstituted composition, and (c) administering the reconstituted composition to the human such that the antibody binds to CANAG present on the surface of the cell and the cytotoxicity of the maytansinoid is activated, whereby the cell is killed.

68. The lyophilized composition of claim 33, wherein the composition comprises (i) a therapeutically effective amount of a conjugate comprising humanized antibody huC242 that binds to CANAG wherein the antibody is chemically coupled to DM4 (ii) about 0.3 mg a buffering agent selected from the group consisting of sodium citrate, sodium acetate, and sodium succinate per mg of the conjugate, (iii) about 0.02 mg of polysorbate 20 or polysorbate 80 per mg of the conjugate, (iv) about 1 mg of sucrose per mg of the conjugate, and (v) about 3.8 mg of glycine per mg of the conjugate, wherein the composition has a pH of about 5.5 when reconstituted with water.

69. A method for killing a cell in a human comprising (a) providing the lyophilized composition of claim 68, (b) adding water to the lyophilized composition to provide a reconstituted composition, and (c) administering the reconstituted composition to the human such that the antibody binds to CANAG present on the surface of the cell and the cytotoxicity of the maytansinoid is activated, whereby the cell is killed.

70. The lyophilized composition of claim 60, wherein the composition comprises (i) a therapeutically effective amount of a conjugate comprising humanized antibody huC242 that binds to CANAG wherein the antibody is chemically coupled to DM1 (ii) about 0.3 mg of a buffering agent selected from the group consisting of sodium citrate, sodium acetate, and sodium succinate per mg of the conjugate, (iii) about 1 mg of sucrose per mg of the conjugate, and (iv) about 3.8 mg of glycine per mg of the conjugate, wherein the composition has a pH of about 5.5 when reconstituted with water.

71. A method for killing a cell in a human comprising (a) providing the lyophilized composition of claim 70, (b) adding water to the lyophilized composition to provide a reconstituted composition, and (c) administering the reconstituted composition to the human such that the antibody binds to CANAG present on the surface of the cell and the cytotoxicity of the maytansinoid is activated, whereby the cell is killed.

72. The lyophilized composition of claim 60, wherein the composition comprises (i) a therapeutically effective amount of a conjugate comprising humanized antibody huC242 that binds to CANAG wherein the antibody is chemically coupled to DM4 (ii) about 0.3 mg of a buffering agent selected from the group consisting of sodium citrate, sodium acetate, and sodium succinate per mg of the conjugate, (iii) about 1 mg of sucrose per mg of the conjugate, and (iv) about 3.8 mg of glycine per mg of the conjugate, wherein the composition has a pH of about 5.5 when reconstituted with water.

73. A method for killing a cell in a human comprising (a) providing the lyophilized composition of claim 72, (b) adding water to the lyophilized composition to provide a reconstituted composition, and (c) administering the reconstituted composition to the human such that the antibody binds to CANAG present on the surface of the cell and the cytotoxicity of the maytansinoid is activated, whereby the cell is killed.

74. The lyophilized composition of claim 60, wherein the maytansinoid is DM1.

75. The lyophilized composition of claim 60, wherein the maytansinoid is DM4.

76. The lyophilized composition of claim 60, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

77. The lyophilized composition of claim 60, wherein the composition comprises about 0.3 mg sodium succinate buffer per mg of the conjugate.

78. The ivophilized composition of claim 60, wherein the composition comprises about 1 mg sucrose per mg of the conjugate.

79. The ivophilized composition of claim 60, wherein the composition comprises about 3.8 mg glycine per mg of the conjugate.

80. A method for killing a cell in a human comprising (a) providing the lyophilized composition of claim 60, (b) adding water to the lyophilized composition to provide a reconstituted composition, and (c) administering the reconstituted composition to the human such that the antibody binds to CANAG present on the surface of the cell and the cytotoxicity of the maytansinoid is activated, whereby the cell is killed.

81. The method of claim 80, wherein the cell is a tumor cell.

82. The method of claim 80, wherein the maytansinoid is DM1.

83. The method of claim 80, wherein the maytansinoid is DM4.

84. The method of claim 80, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

85. The method of claim 80, wherein the concentration of the conjugate in the reconstituted composition is about 0.1 mg/mL to about 5 mg/mL.

86. The method of claim 85, wherein the concentration of the conjugate in the reconstituted composition is about 1 mg/mL.

87. The method of claim 85, wherein the concentration of the conjugate in the reconstituted composition is about 5 mg/mL.

88. The method of claim 80, wherein the concentration of the buffering agent in the reconstituted composition is about 2 mM to about 50 mM.

89. The method of claim 80, wherein the reconstituted composition comprises about 10 mM sodium succinate, and the pH of the reconstituted composition is about 5.5.

90. The method of claim 80, wherein the concentration of sucrose in the reconstituted composition is about 0.1% to about 3% of the total volume of the reconstituted composition.

91. The method of claim 90, wherein the concentration of sucrose in the reconstituted composition is about 0.5% of the total volume of the reconstituted composition.

92. The method of claim 80, wherein the concentration of glycine in the reconstituted composition is about 50 mM to about 500 mM.

93. The method of claim 92, wherein the concentration of glycine in the reconstituted composition is about 250 mM.

94. The method of claim 80, wherein the reconstituted composition is administered to the human intravenously, intraperitoneally, or intratumorally.

95. A composition comprising (i) about 0.1 mg/mL to about 5 mg/mL of a conjugate comprising humanized antibody huC242 that binds to CANAG wherein the antibody is chemically coupled to a maytansinoid that is $N^{2'}$-deacetyl-$N^{2'}$-(3-mercapto-1-oxopropyl)-maytansine (DM1) or $N^{2'}$-deacetyl-$N^{2'}$-(4-mercapto-4-methyl-1-oxopentyl)-maytansine (DM4), (ii) about 2 mM to about 50 mM of a buffering agent selected from the group consisting of sodium citrate, sodium acetate, and sodium succinate, (iii) about 50 mM to about 500 mM sodium chloride, and (v) water, wherein the composition has a pH of about 5-6.

96. The composition of claim 1, wherein the composition has a pH of about 5.5.

97. The method of claim 21, wherein the composition has a pH of about 5.5.

98. The lyophilized composition of claim 33, wherein the composition has a pH of about 5.5 when reconstituted with water.

99. The method of claim 42, wherein the reconstituted composition has a pH of about 5.5.

100. The lyophilized composition of claim 60, wherein the composition has a pH of about 5.5 when reconstituted with water.

101. The method of claim 80, wherein the reconstituted composition has a pH of about 5.5.

102. The composition of claim 1, wherein the concentration of the conjugate in the composition is about 1 mg/ml to about 5 mg/ml.

* * * * *

UNITED STATES PATENT AND TRADEMARK OFFICE
CERTIFICATE OF CORRECTION

| | |
|---|---|
| PATENT NO. | : 7,514,080 B2 |
| APPLICATION NO. | : 11/520878 |
| DATED | : April 7, 2009 |
| INVENTOR(S) | : Amphlett et al. |

It is certified that error appears in the above-identified patent and that said Letters Patent is hereby corrected as shown below:

TITLE PAGE, ITEM (56)

Column 2 under OTHER PUBLICATIONS, "Roguska et al., *Proc. Natl. Acad. Sci.,* 969-973 (1994)" should read -- Roguska et al., *Proc. Natl. Acad. Sci.,* 91, 969-973 (1994) --

IN THE CLAIMS

Claim 21, column 25, line 16, "polysorbate 9" should read -- polysorbate 20 --

Claim 29, column 25, line 42, "vitamin B" should read -- vitamin E --

Claim 51, column 26, line 53, "comprises 10 mM" should read -- comprises about 10 mM --

Claim 64, column 27, line 53, "comprises (i) 0.1 mg/mL" should read -- comprises (i) about 0.1 mg/mL --

Claim 65, column 27, line 63, "(i) about 0.1 mg/mL mg/mL" should read -- (i) about 0.1 mg/mL --

Claim 66, column 28, line 9, "(ii) about 0.3 mg a buffering agent" should read -- (ii) about 0.3 mg of a buffering agent --

Claim 68, column 28, line 28, "(ii) about 0.3 mg a buffering agent" should read -- (ii) about 0.3 mg of a buffering agent --

Claim 77, column 29, line 20, "sodium succinate buffef" should read -- sodium succinate --

Claim 78, column 29, line 22, "The ivophilized" should read -- The lyophilized --

UNITED STATES PATENT AND TRADEMARK OFFICE
CERTIFICATE OF CORRECTION

PATENT NO.        : 7,514,080 B2
APPLICATION NO.   : 11/520878
DATED             : April 7, 2009
INVENTOR(S)       : Amphlett et al.

It is certified that error appears in the above-identified patent and that said Letters Patent is hereby corrected as shown below:

Claim 79, column 29, line 25, "The ivophilized" should read -- The lyophilized --

Signed and Sealed this

Twenty-third Day of June, 2009

JOHN DOLL
*Acting Director of the United States Patent and Trademark Office*